United States Patent [19]

Cherwonogrodzky et al.

[11] Patent Number: 5,006,463

[45] Date of Patent: Apr. 9, 1991

[54] IMMUNOASSAYS FOR DISCRIMINATING BETWEEN BRUCELLOSIS INFECTIONS AND VACCINATIONS

[75] Inventors: John W. Cherwonogrodzky, Kanata; J. Robert Duncan, Nepean; Klaus Nielsen; Peter F. Wright, both of Richmond; David R. Bundle; Malcolm B. Perry, both of Ottawa, all of Canada

[73] Assignee: National Research Council of Canada, Ottawa, Canada

[21] Appl. No.: 100,873

[22] Filed: Sep. 25, 1987

[30] Foreign Application Priority Data

Sep. 26, 1986 [CA] Canada .................................. 519243

[51] Int. Cl.[5] .................. G01N 33/53; G01N 33/543; G01N 33/531; C12Q 1/04

[52] U.S. Cl. .................................... 435/7.32; 424/92; 435/34; 435/101; 435/174; 435/810; 435/822; 436/501; 436/518; 436/543; 436/808; 436/809; 436/811; 530/350; 530/812; 530/825

[58] Field of Search ...................... 435/7, 34, 38, 101, 435/822, 810, 174, 176, 177; 436/501, 518, 543, 809, 808, 811, 822; 424/92; 530/350, 812, 825

[56] References Cited

U.S. PATENT DOCUMENTS

| | | | |
|---|---|---|---|
| 4,281,061 | 7/1981 | Zuk et al. | 435/7 |
| 4,652,518 | 3/1987 | Makeia et al. | 435/7 |

FOREIGN PATENT DOCUMENTS

| | | |
|---|---|---|
| 1054516 | 5/1979 | Canada . |
| 1212051 | 9/1986 | Canada . |
| 2524315 | 4/1983 | France . |
| 938944 | 6/1982 | U.S.S.R. . |

OTHER PUBLICATIONS

T. J. G. Raybould et al., Serological Differentiation between Infected and Vaccinated Cattle, 1979, pp. 37–46, Journal of Immunological Methods, vol. 30.

T. J. G. Raybould et al., Serological Differentiation between Infected and Vaccinated Cattle, 1980, pp. 435–441, Infection and Immunity, vol. 29, No. 2.

Ramon Diaz et al., Radial Immunodiffusion Test with a Brucella Polysaccharide Antigen, 1979, pp. 37–41, Journal of Clinical Microbiology, vol. 10, No. 1.

R. Diaz et al., Studies on the Polysaccharide B and Native Haptene, 1984, pp. 213–220, Develop. Biol. Standard, vol. 56.

Lois M. Jones et al., Evaluation of a Radial Immunodiffusion Test with Polysaccharide B Antigen, 1980, pp. 753–760, Journal of Clinical Microbiology, vol. 12.

Edgardo Morena et al., Immunochemical Characterization of Brucella Lipopolysaccharides, 1981, pp. 214–222, Infection and Immunity, vol. 31, No. 1.

L. Fernandez-Lago et al., Immunological Identity of Brucella Native Hapten, 1982, pp. 778–780, Infection and Immunity, vol. 38, No. 2.

Caroff et al., Chemical Abstracts, vol. 102, Abstract No. 439992, 1985.

Bundle et al., Chemical Abstracts, vol. 101, Abstract No. 228245y, 1984.

Berman et al., Chemical Abstracts, vol. 93, Abstract No. 24087e.

Perry et al., Chemical Abstracts, vol. 104, Abstract No. 184483e, 1986.

*Primary Examiner*—Esther L. Kepplinger
*Assistant Examiner*—Florima G. Hoffer
*Attorney, Agent, or Firm*—Sughrue, Mion, Zinn, Macpeak & Seas

[57] ABSTRACT

A method is disclosed for discriminating between cattle vaccinated against and those infected with Brucella spp. The method involves immunoassay using a purified polysaccharide containing 4,6-dideoxy-4-acylamido-D-mannopyranosyl units obtained from *B. abortus* or from cross-reacting organisms, and results in improved differentiation between vaccinated and infected animals. Test kits are also disclosed for performing the assay and a process is disclosed for obtaining the O-chain polysaccharides in high purity and yield.

13 Claims, 1 Drawing Sheet

IMMUNOASSAYS FOR DISCRIMINATING BETWEEN BRUCELLOSIS INFECTIONS AND VACCINATIONS

FIELD OF THE INVENTION

This invention relates to a method of immunoassay for discrimination between animals vaccinated against and those infected with *Brucella spp.*

BACKGROUND OF THE INVENTION

*Brucella* is a genus of Gram-negative bacteria which are the causative agents of brucellosis, an important disease of animals and humans. In animals, for example cattle, brucellosis causes abortions and in addition decreased meat and milk production. In humans, it produces intermittent debilitation with high fever which may resist antibiotic therapy and recur over a period of several years. The disease can therefore be the cause of serious health problems and substantial economic losses.

The species *B. abortus*, which is one example of this genus, remains a problem throughout the world. In South American countries, for example, up to 40% of cattle herds are affected by brucellosis, thousands of human cases are known, and economic losses are estimated at tens of millions of dollars annually. Other economically significant species include *B. melitensis* (which affects humans, sheep and goats), *B. suis* (which affects pigs, reindeer and humans), *B. ovis* (affecting sheep) and *B. canis* (affecting dogs and humans).

There have been advances in the development of vaccines against brucellosis. For example, in the case of *B. abortus*, there is common use of an attenuated live strain (S19) of *B. abortus*. However, two problems persist. The first is that, although the vaccine is effective, the protection it affords is not absolute, hence allowing some infection by field strains of *B. abortus*. The second problem is that, with current diagnostic techniques, vaccinated animals appear serologically similar to those infected. In Canada, limited vaccination of cattle by *B. abortus* S19 still occurs for export purposes. In the United States, 2.9 million cattle were vaccinated in 1985, in part because some of the southern states (Texas, Florida, Louisiana and Arkansas) still have high prevalences of brucellosis in their cattle populations. There is therefore an urgent need for a method of discriminating vaccinated from infected cattle.

To date, some discrimination is possible by setting limits for the amount of antibody against *B. abortus* produced using whole smooth-lipopolysaccharide (sLPS) complex in enzyme immunoassay (EIA or ELISA). FIG. 1 depicts graphically the distribution of cattle sera with antibodies having affinity or specificity for this antigen in one case study. In the Figure, the frequency or number of cattle, is plotted against the lower class limit (i.e. five sera with $A_{414nm}$ on the enzyme immunoassay of 1.00, 1.01, 1.02, 1.03 and 1.04 would be represented by a bar at 1.00 having a frequency of 5 sera). It can be seen that, in general, the vaccinates have readings below an $A_{414nm}$ of 0.50, while culture positives (i.e. *B. abortus* was isolated from these animals) have sera that gave an $A_{414nm}$ above 0.50 on this test. However, there is still considerable overlap, mostly in the 0–0.50 range but also some degree of overlap at higher readings (note the high positive readings of vaccinate sera around $A_{414nm}$ of 1.5).

The difficulty in differentiating vaccinates from infected cattle is again evident in a study that compared the sensitivities and specificities of five serodiagnostic tests used for the detection of bovine antibodies to *B. abortus*. The results of this study are given in the following Table 1.

TABLE 1

COMPARATIVE ASSAY RESULTS

| Status of Cattle | Number of Cattle | Number of Positive Readings | | | | |
|---|---|---|---|---|---|---|
| | | BPAT[1] | STAT[2] | CFT[3] | HIGT[4] | EIA[5] |
| FREE LISTED[a] | | | | | | |
| 1 non-vaccinated | 1067 | 12 (1.1%) | 6 (0.6%) | 0 (0%) | 0 (0%) | 1 (0.1%) |
| 2 vaccinated | 76 | 6 (7.8%) | 2 (2.6%) | 0 (0%) | 8 (10.5%) | 3 (3.9%) |
| REACTOR[b] | | | | | | |
| 1 non-vaccinated | 798 | 74 (9.3%) | 50 (6.3%) | 9 (1.1%) | 4 (0.5%) | 5 (0.6%) |
| 2 vaccinated | 253 | 20 (7.9%) | 15 (5.9%) | 5 (2.0%) | 12 (4.7%) | 14 (5.5%) |
| INFECTED[c] | | | | | | |
| 1 positive | 174 | 152 (87.4%) | 162 (93.1%) | 159 (91.4%) | 167 (96.0%) | 162 (93.1%) |

[1]BPAT = buffered plate antigen test
[2]STAT = standard tube agglutination test
[3]CFT = complement fixation test
[4]HIGT = hemolysis-in-gel test
[5]EIA = enzyme immunoassay
[a]Free listed = cattle from herds certified in the previous year as being of brucellosis based on standard serological tests.
[b]Reactor = cattle from herds containing two or more positive reactors based on standard serological tests, but herds in which no infected cattle have been indentified based on bacteriological culture.
[c]Infected = cattle identified as infected by positive bacteriological culture Table 1 shows that the buffered plate antigen test (BPAT, which is currently used as a screening test) recorded 1.1% of non-vaccinated and 7.8% of vaccinated cattle in *Brucella*-free herds as positive. The enzyme immunoassay (EIA, for further details see Nielsen and Wright, 1984, Agriculture Canada publication, ISBN 0-662-13421-4) greatly reduces the number of false-positive non-vaccinated cattle to 0.1% but the number for vaccinates remains high at 3.9%. The other serological tests show similar limitations. The complement fixation test (CFT) is an exception by having high specificity but its costs and technical manipulations make it unlikely to remain a routine method. Table 1 also shows that problem herds (those that persistently show reactors for no apparent cause) have a high number of false-positives for non-vaccinated and vaccinated cattle (i.e. 0.6% and 5.5% respectively for the EIA).

From the above data, it can be seen that present serodiagnostic tests are for the most part effective in discriminating *Brucella*-free from infected cattle. However, there is a small percentage of animals in the intermediate range (e.g. vaccinates with high titres or infected cattle with low titres of antibodies) that are impossible to classify reliably by standard serological methods. A small percentage of several million cattle is still a large population and since these animals may be highly valued, there is a great need for a test that will differentiate vaccinated cattle from *B. abortus* infected cattle.

T. J. G. Raybould and Shireen Chantler, J. Immunol. Methods, 30 (1979) pages 37–46 describe an immunofluorescent procedure in which antigenic extracts of *B. abortus* 544/W were coupled to Sepharose® beads. The crude sodium dodecyl sulfate (SDS) extract contained polysaccharide, lipopolysaccharide, proteins, etc., and when coupled to the Sepharose® beads showed discrimination between vaccinated and infected cattle, with, however, some overlap of results. In subsequent work (Raybould et al., Infect. Immun. 29 (1980) pages 435–441), they determined from inspection of the SDS extract that the active group for the discrimination was an antigen "X". As it bound to oxidised Sepharose®, they concluded that antigen "X" contained amino groups and hence was a basic protein. The test given in that report involved hemagglutination, gave some overlap similar to that seen in other tests and in some instances was inconclusive.

It has also been reported (Diaz, R., P. Garatea, L. M. Jones, and I. Moriyon, 1979, Radial diffusion test with a Brucella polysaccharide antigen for differentiating infected from vaccinated cattle, J. Clin. Microbiol. 10:37–41; Jones, L. M., D. T. Berman, E. Moreno, B. L. Deyoe, M. J. Gilsdorf, J. D. Huber, and P. Nicoletti, 1980, Evaluation of a radial immunodiffusion test with polysaccharide B antigen for diagnosis of bovine brucellosis, J. Clin. Microbiol. 12:753–760), that there is a component of *Brucella melitensis*, termed "poly B" which can differentiate vaccinated from infected cattle, i.e. only the sera of the latter will precipitate "poly B" in agar gel immunodiffusion (or AGID). "Poly B" has been characterized by Moreno, E., S. L. Speth, L. M. Jones, and D. T. Berman, 1981, Immunochemical characterization of Brucella lipopolysaccharides and polysaccharides, Infect. Immun. 31:214–222, as a polysaccharide consisting primarily of glucose units. Our studies support these findings and we have now isolated "poly B" from *B. melitensis* 16M and found it to be essentially a polymer of glucose molecules. Some sera of infected cattle will react weakly with this component in AGID provided that 10% NaCl is added to the buffer (0.1 M sodium borate, pH 8.3). However, we have observed that while the principal component, "poly B" (the glucose polymer) is a poor antigen; the associated minor component, O-chain polysaccharide (containing 4,6-dideoxy-4-formamido-D-mannopyranose), is the immunodominant or "active ingredient" in these preparations. We have also found that reports of immunological identify between the O-chain polysaccharide and "poly B", the glucose polymer, (Moreno et al., 1981, Infect. Immun. 31; 214–222, Fernandez-Lago et al., 1982, Infect. Immun. 38, 778–780) were likely due to the latter containing O-chain as an impurity.

SUMMARY OF THE INVENTION

It is therefore an object of the present invention to provide an improved method of differentiating between animals (e.g. cattle) which have been vaccinated and those infected with *Brucella* species based on serological activity of their sera on polysaccharide (e.g. O-chain).

Another object of the invention is to provide a test kit for carrying out a discrimination between animals vaccinated or immunized against *Brucella* species by an indirect or competitive immunoassay.

A further object is to provide methods of isolating the discriminating antigen, O-chain polysaccharide, which afford higher yields, within a relatively shorter time and in greater purity than conventional methods.

Accordingly, one aspect of the invention provides a method of discriminating animals, for example cattle, vaccinated or immunized against a *Brucella sp.*, such as *B. abortus*, from those infected with the *Brucella sp.*, which comprises subjecting serum samples from the animals to an immunoassay using an antigen containing 4,6-dideoxy-4-acylamido-D-mannopyranose repeating units, and thereafter differentiating the sera of the vaccinates from those of infected animals based on a negative or positive result, respectively, of said assay. The polysaccharide is preferably present as O-chain.

The term "acylamido" includes, for example, formamido, acetamido, propionamido and butyramido.

A particular aspect of the invention provides a method of discriminating between cattle vaccinated or immunized against *Brucella abortus* and those infected with *B. abortus*, which comprises subjecting sera from the cattle to enzyme immunoassay using a purified O-chain polysaccharide of *B. abortus* containing 4,6-dideoxy-4-formamido-D-mannopyranose repeating units, and thereafter differentiating the sera of vaccinates from those of infected animals based on a respective negative or positive result of the assay.

Another aspect of the invention provides a test kit for carrying out an immunoassay for discriminating between animals, such as cattle, vaccinated or immunized against a *Brucella* species, such as *B. abortus* and those infected with the species, which comprises:

(a) a support carrying antigenic polysaccharide (e.g. as O-chain) containing 4,6-dideoxy-4-acylamido-D-mannopyranose units; and (b) an immunological detection system for discriminating between the presence or absence of antibodies against *Brucella sp.*

The kit operates in conjunction with a source of antibody, which can be a polyclonal source, i.e. animal sera, or a monoclonal source, i.e. from monoclonal hybridomas.

The term "immunoassay" is intended to cover any assay format involving serological determination, including, for example, enzyme immunoassay (e.g. ELISA), competitive immunoassay, radioimmunoassay, immunofluorescent assay, and immunoassays using polystyrene plates, membranes, dipsticks or beads.

The term "immunized" as used herein embraces immunization with whole cells of *Brucella* species, with cross-reacting organisms, extracts of said cells and organisms, synthetic antigens, derived antigens and gene products.

DETAILED DESCRIPTION OF THE INVENTION

Figure 1:
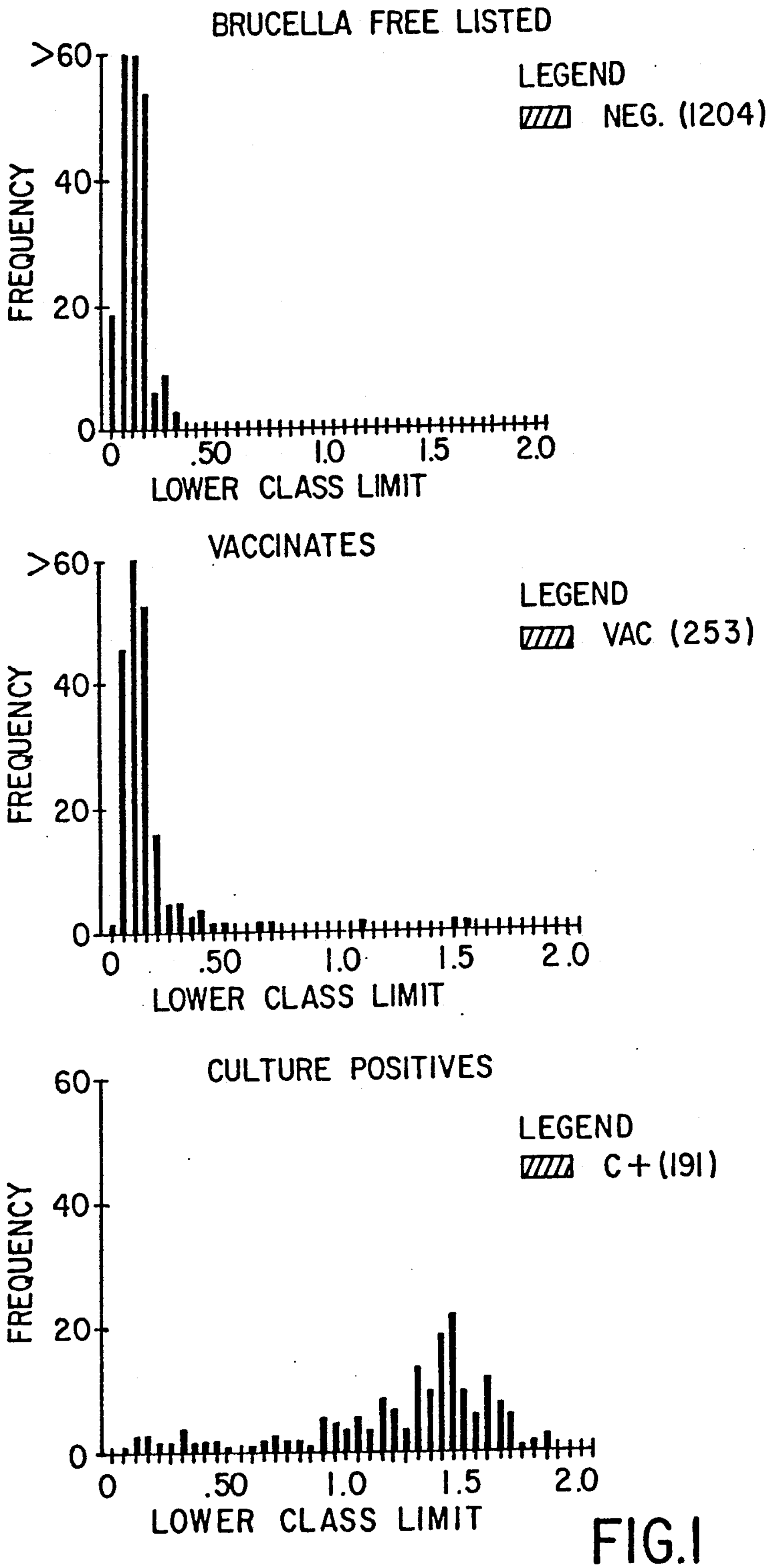

Analysis of a preparation of the "poly B" (prepared by the method of Diaz) referred to above reveals that it is predominantly the glucose polymer noted above. However, NMR-spectroscopy studies have shown that this preparation also contained small amounts of a polysaccharide containing 4,6-dideoxy-4-formamido-D-mannopyranose units of the formula:

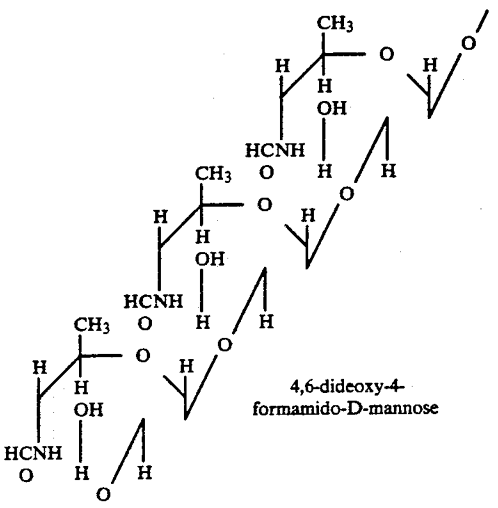

4,6-dideoxy-4-formamido-D-mannose

Polysaccharides of this type are described in copending Canadian Patent Application Ser. No. 448,768, filed March 2, 1984.

Our AGID studies show that the preparation gave two precipitin lines (one strong and the other faint) with sera of infected animals. The prominent precipitin line gave a line of identity with the sLPS of *B. abortus* 1119-3, *B. melitensis* 16M and *Yersinia enterocolitica* 0:9. The only component known to be common to these is their 0-chain polysaccharide which contains 4,6-dideoxy-4-formamido-D-mannopyranose repeating units. The precipitin line did not occur if the sera were cross-absorbed with *Y. enterocolitica* 0:9 cells. Therefore, the main antigenic component and the one giving discrimination of animals is the 4,6-dideoxy-4-formamido-D-mannopyranose polymer.

We have now determined that the purified O-chain containing 4,6-dideoxy-4-formamido-D-mannopyranose units, from *B. abortus* (e.g. strains 1119-3 and 413) can differentiate sera of vaccinated from infected animals, e.g., cattle, by immunoassay techniques, for example by either AGID or ELISA (recommended O-chain concentrations are 1 mg/ml for AGID and 2.5 μg/ml for ELISA). The O-chains of *B. melitensis* 16M and *Yersinia enterocolitica* 0:9 are also effective for this purpose, although for the ELISA care must be exercised in preparing the solid phase for the assay. Both *Y. enterocolitica* 0:9 and *B. melitensis* (e.g. strain 16M) have O-chains of 4,6-dideoxy-4-formamido-D-mannopyranose as does *B. abortus*. Monoclonal antibodies (e.g. clones Ys-T9-3 and Ys-T9-7) as described in Canadian Patent Application No. 448,768 suggest that some small differences may exist between the O-chains (of *B. abortus*, *B. melitensis* and *Y. enterocolitica*), but this has not been rigorously proven.

In the past, the O-chain polysaccharide of *B. abortus* has been difficult to purify, yielding at best about 100 mg of polysaccharide from 100 g wet weight of cells (Caroff et al., 1984, Infect. Immun. 46:384) and most often yielding far less than this amount. We have developed rapid methods which consistently give higher yields (e.g. about 500 mg of O-chain from 100 g wet weight of cells by one method, and about 330 mg of purified O-chain in a few hours by another method).

Accordingly, a further aspect of the invention provides a method of isolating polysaccharide containing 4,6-dideoxy-4-formamido-D-mannopyranose units from *Brucella sp.* which comprises (a) heating a suspension of whole cells or a crude extract thereof in an acidic salt solution;

(b) separating the supernatant from the cellular debris; and (c) extracting the O-chain polysaccharide therefrom by precipitating out contaminants and/or subjecting the supernatant to partitioning.

Partitioning can be accomplished using phenol-water extraction in which the O-chain sequesters into the phenol layer. Increased yield of O-chain is obtained when the supernatant from step (b) is neutralized and dialyzed against buffer, then treated with enzymes that degrade contaminants.

A preferred method of isolating the O-chain polysaccharide comprises:

(a) suspending killed cells of *B. abortus* in TRIS-saline, washing and resuspending the cells in acetic acid and sodium chloride solution, (b) heating and centrifuging the suspension, (c) extracting the supernatant and treating it with lysozyme, ribonuclease, deoxyribonuclease and proteinase followed by dialysis against TRIS-saline, (d) extracting the product with phenol/water and dialyzing the phenol layer against TRIS-saline, and (e) extracting and separating the supernatant.

A particular embodiment of this method is set out in tabular form in the following Table 2.

TABLE 2

PURIFICATION OF O-CHAIN POLYSACCHARIDE FROM BRUCELLA ABORTUS 1119-3

1. Cells killed and suspended in TRIS-saline (1% NaCl, 0.02% $NaN_3$, 0.12% TRIS-HCl, pH 7) with 2% pheno. Wash and resuspend cells (100 g cells/500 ml) in 2% (vol/vol) acetic acid and 10% NaCl.
2. Autoclave at 15 psi and 121° C. for 30 minutes (sealed centrifuge bottles).
3. Centrifuge at 20,000 X g for 30 minutes at 4° C. Save supernatant, neutralize with NaOH. Precipitate with 5 volumes methanol with 1% sodium acetate. Redissolve and dialyze against TRIS-saline.
4. Digest in 25 μg/ml lysozyme, ribonuclease and deoxyribonuclease for 6 hours Digest in 50 μg/ml proteinase K for 48 hours Dialyze against TRIS-saline.
5. Do phenol-water extraction (room temperature). Remove phenol layer, precipitate polysaccharide with methanol plus 1% sodium acetate, dialyze against TRIS-saline.
6. Ultra-centrifuge 100,000 X g for 18 hours at 4° C. Save supernatant (700 mg O-chain).
7. Lyophilize, redissolve in 0.05 M pyridinium acetate (4 ml). Sephadex® G-50 column chromatography (column size 2.5 cm diameter×100 cm height). Lyophilize first peak (500 mg O-chain).

Thus, for obtaining O-chain polysaccharide from cells of *Brucella sp.*, the following general principles obtain:

(a) The O-chain polysaccharide can be released from purified smooth-lipopolysaccharide with acid and heat (Caroff et al., 1984, Inf. Immun. 46; 384–388; Canadian Patent Application Ser. No. 448,768). We have now observed that such release will occur from whole cells as an initial step. If the cells (or crude extract thereof) are suspended in high salt concentrations (e.g. 10% NaCl) and weak acid (e.g. 2% acetic acid), then heated (e.g. autoclaved), a large amount of O-chain polysaccharide is released with reduced contamination (e.g. protein) than conventional methods. Cellular debris can be removed (e.g. by centrifugation).

(b) A rapid yield of O-chain polysaccharide can be acquired from the above by (i) precipitating contaminants (e.g. proteins, oligonucleotides) with agents (such as trichloracetic acid) and removing these precipitates (e.g. by centrifugation);

(ii) partitioning (e.g. by phenol-water extraction) in which the O-chain sequesters into one layer (phenol) while other contaminants sequester into the other layer (e.g. water); and (iii) removal of low-molecular contaminants (e.g. by the method of dialysis).

(c) Increased yields of O-chain were observed when crude extracts (e.g. supernatant of part a, above) were neutralized and dialyzed against buffer then treated with enzymes that degrade contaminants.

(d) precipitation of the O-chain (e.g. at least 5 volumes with methanol plus 1% sodium acetate) greatly conserved reagents and made purification more manageable. Precipitating O-chain or sLPS in phenol with the use of alcohol (e.g. at least 5 volumes methanol plus 1% sodium acetate), followed by resuspension and reprecipitation in this alcohol, removes the phenol without adversely affecting the antigen.

Another embodiment of the above procedure is set out in the following Table 3.

TABLE 3

RAPID PURIFICATION OF O-CHAIN POLYSACCHARIDE

FROM BRUCELLA ABORTUS 1119-3

1. Either killed or live cells are washed and resuspended (100 g wet weight of cells/500 ml) in 2% (vol/vol) acetic acid and 10% NaCl solution.
2. Autoclave at 15 psi, 121° C. for 20 minutes (in sealed Nalgene ® centrifuge bottles). Open bottles, place in water-bath and cool.
3. Centrifuge at 8,000×g for 20 minutes at 4° C. Save the supernatant and neutralize with NaOH. To the remaining cell pellet, resuspend in 2% acetic acid, 10% NaCl (about 200 ml for 100 g cells), centrifuge and add this supernatant to the other. Neutralize with NaOH.
4. Precipitate with 5 volumes pre-chilled (ice-bath) methanol plus 1% sodium acetate. Chill in an ice-bath, with occasional mixing, for about an hour. Centrifuge, save the pellet and redissolve this in 20 ml distilled water. Add 100 ml of 0.3 M trichloroacetic acid (pre-chilled at 4° C. Stir in refrigerator (4° C.) for 1 hour. Centrifuge and save the supernatant. Adjust pH to 7 with NaOH.
5. Precipitate with 5 volumes pre-chilled (ice-bath) methanol plus 1% sodium acetate. Centrifuge and dissolve the pellet in about 100 ml distilled water. Add an equal volume of 95% phenol. Stir at room temperature for about 30 minutes. Centrifuge and save phenol layer. Add to the phenol layer another 100 ml of distilled water, stir at room temperature for 30 minutes, centrifuge and save phenol layer.
6. Take the phenol layer, add 5 volumes pre-chilled methanol plus 1% sodium acetate, chill in an ice-bath for 1 hour with occasional mixing. Centrifuge, save pellet. Resuspend pellet in an equal volume of pre-chilled methanol plus 1% sodium acetate (i.e. high speed magnetic stirring so that suspension is complete and phenol is removed). Centrifuge, save pellet. Dissolve pellet in distilled water (if desired, remove sodium acetate by dialysis). Lyophilize.

Time elapsed: 1 work day Yield: 330 mg O-chain from 100 g wet weight of cells.

The method for the ELISA is described in the following Table 4.

TABLE 4

INDIRECT ELISA FOR DETECTION OF BOVINE SERUM

ANTIBODY TO B. ABORTUS O-CHAIN POLYSACCHARIDE

1. Prepare a 2.5 μg/ml solution of O-chain polysaccharide (or 1 g/ml LPS) in coating buffer (0.06μM sodium carbonate buffer, pH 9.6). Dispense 200 μl volumes in all wells of polystyrene plates which have been previously rinsed with distilled water. Seal plates and incubate overnight (ca. 18h) at room temperature (ca. 22° C).
2. The following day, prepare dilutions of test samples and controls in wash/diluent buffer (0.85% NaCl, 0.01 M sodium phosphate, pH 7.2 plus 0.05% Tween ® 20). All dilutions should be prepared and maintained at room temperature.
3. Immediately prior to sample application, wash with equal efficiency all wells of the antigen-coated plate with wash/diluent buffer. After four consecutive washes, discharge residual buffer by inverting plate and vigorously rapping onto a lint-free absorbent surface.
4. Dispense 200 μl volumes of serum samples in microtiter wells, seal the plate and incubate for 3 hours at room temperature.
5. Prepare a working dilution of conjugate (e.g. rat monoclonal anti-bovine (H & L) IgG conjugated with horseradish peroxidase) in wash/diluent buffer. Wash polystyrene plate as described in Step 3, then dispense 200 μl volumes of conjugate to all wells, seal the plate and incubate for 1 hour at room temperature.
6. Prepare a working solution of enzyme substrate (0.015% $H_{202}$, 1mM ABTS, in 0.05 M citrate, pH 5.0 with NaOH). Wash polystyrene plate as described in Step 3, dispense 2 volumes of substrate to all wells in the polystyrene plate and immediately begin timing the reaction with a stop watch. Incubation should be on a plate shaker at room temperature.
7. At the end of incubation (e.g. 10 minutes), the $A_{414nm}$ by a photometric polystyrene plate scanner should be read Target control sera and mean $A_{414nm}$ of duplicate test samples are used to determine seropositive or seronegative status based on a threshold $A_{414nm}$ determined by seroepidemiological methods (e.g. positive is ≧0.300).

The results for one immunoassay are shown by testing cattle sera by enzyme immunoassay using both the *B. abortus* sLPS and O-chain polysaccharide as shown in the following Table 5.

TABLE 5

Comparison by Enzyme Immunoassay of Cattle Sera Binding to *Brucella abortus* smooth-lipopolysaccharide and to 0-chain polysaccharide

| Sera | Dilution | Antigen sLPS (1 μg/ml) | 0-chain (2.5 μg/ml) |
|---|---|---|---|
| 1 Negative Controls | | | |
| #280[a] | 1:100 | 0.11[b] | 0.09 |
| #281 | 1:100 | 0.11 | 0.10 |
| #282 | 1:100 | 0.21 | 0.10 |
| Conjugate Control[c] | | 0.10 | 0.10 |
| 2 Vaccinates (bled 28 days post-vaccination) | | | |
| #679 | 1:100 | 2.03 | 0.15 |
| #743 | 1:100 | 2.31 | 0.21 |
| #1066 | 1:100 | 0.70 | 0.08 |
| 1429 | 1:100 | 1.80 | 0.09 |
| 3 Infected | | | |
| #25 | 1:12800 | 0.90 | 0.55 |
| #908 | 1:800 | 2.19 | 0.59 |
| #950 | 1:12800 | 1.43 | 0.45 |
| #CF80 | 1:200 | 2.29 | 0.59 |

[a]Laboratory designation
[b]$OD_{414nm}$ on an enzyme immunoassay (readings 0.3 are positive)
[c]Conjugate control = rat anti-bovine antibody conjugated with horseradish peroxidase It can be seen that, upon testing cattle sera by using the whole SLPS complex from *B. abortus* as antigen on polystyrene plates in an enzyme immunoassay, there appeared to be little differentiation between high titre sera of vaccinated and infected cattle. However, when the O-chain polysaccharide of *B. abortus* prepared as described above is applied, considerable differentiation can be made. Table 5 shows that sera from either vaccinated or infected cattle with high antibody titres against *Brucella abortus* will both give positive readings with an enzyme immunoassay using polystyrene plates coated with *B. abortus* sLPS. However, if the above-obtained *B. abortus* O-chain polysaccharide is used as the antigen, then sera from infected cattle (identified as positive in the test) can be differentiated from the sera of vaccinated cattle (identified as negative). The mechanism for this differentiation is unclear but Table 5 suggests that the antibodies of infected cattle have a different specificity or affinity than those of vaccinated cattle to the presented antigens.

It can be noted that vaccinated-cattle serum #743 at a 1:100 dilution gives a considerably higher positive reading than infected-cattle serum #25 at a 1:12800 dilution when *Brucella abortus* sLPS is used as antigen for the enzyme immunoassay. If these sera had antibodies of the same specificity for *B. abortus* O-chain as for sLPS, then one would expect to observe the same pattern with the results using O-chain. However, at the noted dilutions the reading for vaccinated-cattle serum #743 tested with O-chain should be considerably higher than for infected-cattle serum #25 on the same antigen (bearing in mind the dilution factor). This is not the case. Serum #743 gives instead a low or negative result, serum #25 gives a high or positive reading. Similar comparisons can be seen with other examples in Table 5 (compare vaccinate serum #679 with infected cattle sera #908 and #CF80; vaccinate serum #1429 with infected serum #950).

To date, 100 negative control sera, 50 vaccinates and 25 culture-positive cattle sera have been tested on this system and have given results as noted above. Therefore, it is likely that the antibodies of infected cattle have a higher affinity against O-chain polysaccharide than those of vaccinated cattle which react poorly to this antigen. Also tested were eight vaccinated adult cattle that had received "full dose" inoculation (rather than reduced dose) of *B. abortus* S19, with similar negative results on "O-chain".

As stated previously, discrimination between sera of vaccinated and infected cattle was evident as in the examples of the serological tests of AGID and ELISA. For the former test, if a mixture of O-chain and smooth-lipopolysaccharide (each 1 mg/ml) is placed in a well cut in the agar, sera of infected cattle will precipitate both antigens, sera of vaccinated cattle will precipitate only sLPS (as judged by the appearance of the precipitin lines and lines of identity with a well containing only one antigen). Clearly the affinities or specificities of the two sera groups differ.

For the ELISA, antigen adherence in our system may be due to:

(i) O-chain polysaccharide adherence to polystyrene.

(ii) our O-chain preparation may contain traces of LPS, the latter being the discriminating antigen.

(iii) the antigenic polysaccharide is coupled to a component which in turn binds to polystyrene.

For the first point, we have observed that the 0chain is both hydrophilic (readily dissolves in water) and hydrophobic (sequesters into the phenol phase of a phenol-water extraction). Such properties may account for adherence.

For the second point, different concentrations (ranging from 2 ng/ml to 12.5 μg/ml) of O-chain, sLPS and alkaline-treated (0.2 M NaOH, 70° C., 15 min.) LPS were coated onto plates. Results were similar for 2.5 μg/ml O-chain and 8 ng/ml LPS or alkaline-treated LPS (see the following Table 6). Since the use of low concentrations of LPS preparations in ELISA give some differentiation of vaccinated and infected cattle, we now present this technique as an alternative. However, Table 6 shows that these dilutions of sLPS and alkaline-treated LPS as antigens in the ELISA test gave more false-positives for sera of vaccinated cattle than did O-chain as antigen. Therefore, we recommend the use of O-chain. It should also be noted that when O-chain preparations were tested with Limulus Amebocyte Lysate (Pyrotell ®, Associates of Cape Cod, Inc., Woods Hole, Mass.) there was less than 0.1% LPS detected.

For the third point, samples of O-chain polysaccharide (1 mg/ml) were treated with 0.2 mg/ml lysozyme, deoxyribonuclease, ribonuclease, proteinase for 24 hours (room temperature). Such treatment did not affect ELISA test results and hence indicates that adherence by a contaminant is unlikely.

It should also be noted that in the model of the use of a synthetic antigen (O-chain of *Yersinia enterocolitica* 0:9 coupled to a hydrophobic carrier, as described in Patent Application 448,678; used at 1 μg/ml in the ELISA), similar discrimination of vaccinates and infected cattle occurred as with the use of O-chain. The existence of O-chain coupled to a hydrophobic carrier, as an active ingredient in our preparations, is a possibility.

TABLE 6

| COMPARISON OF DIFFERENT ANTIGENS USED IN THE ELISA | | | |
|---|---|---|---|
| | ANTIGENS | | |
| Sera | O-Chain (2.5 μg/ml) | SLPS (8 ng/ml) | Alkali-Treated (8 ng/ml) |
| 1 Negative Control | | | |
| N1[a] | 0.150[b] | 0.055 | 0.081 |
| N4 | 0.164 | 0.058 | 0.082 |
| N5 | 0.126 | 0.038 | 0.074 |
| N6 | 0.129 | 0.061 | 0.075 |
| 2 Vaccinates | | | |
| 170 | 0.168 | 0.170 | 0.236 |
| 446 | 0.270 | 0.379 | 0.408 |
| 679 | 0.185 | 0.190 | 0.182 |
| 743 | 0.285 | 0.347 | 0.381 |
| 1066 | 0.112 | 0.083 | 0.080 |
| 1426 | 0.267 | 0.298 | 0.396 |
| 1429 | 0.267 | 0.226 | 0.185 |
| 1440 | 0.253 | 0.291 | 0.299 |
| 3 Infected | | | |
| 25 | 0.547 | 0.620 | 0.698 |
| 950 | 0.553 | 0.538 | 0.824 |
| 44/33 | 0.345 | 0.400 | 0.419 |

[a]Laboratory designation

[b] $A_{414nm}$ on an enzyme immunoassay (readings ≧0.3 are positive, false-positive readings are underlined)

Having regard to available sources of *B. abortus* O-chain polysaccharide, both *B. abortus* 1119-3 and 413 contain sLPS with O-chains of 4,6-dideoxy-4-formamido-D-mannopyranose. Upon testing purified O-chains of these two strains, both were comparable in the differentiation of negative, vaccinated and culture-positive cattle sera. The advantage of using the O-chain of *B. abortus* 1119-3 is that from this strain more of this antigen can be isolated than from strain 413 (500 mg for the former and 170 mg for the latter from 100 g wet weight of cells).

Similarly to the above, purified O-chains containing 4,6-dideoxy-4-acylamido-D-mannopyranose, such as from *B. melitensis* 16M and *Y enterocolitica* 0:9 gave similar reactions. Results obtained using *B. abortus* 1119-3 O-chain and *Y. enterocolitica* 0:9 O-chain are set out in the following Table 7.

TABLE 7

| Comparison of Different Antigens[a] | | | | |
|---|---|---|---|---|
| | Labora- | ANTIGEN | | |
| Cattle Test Serum | tory Desig- nation | *B. abortus* 1119-3 sLPS | *B. abortus* 1119-3 O-chain | *Y.enterocolitica* 0:9 O-chain |
| Negative | CI | 0.046[b] | 0.072 | 0.085 |
| | CII | 0.072 | 0.098 | 0.092 |
| | Neg. | 0.098 | 0.157 | 0.108 |
| Vaccinates | 679 | 0.155 | 0.092 | 0.064 |
| | 1429 | 0.245 | 0.077 | 0.100 |
| | 1066 | 0.065 | 0.071 | 0.074 |
| | 446 | 1.694 | 0.144 | 0.081 |
| | 743 | 0.609 | 0.097 | 0.087 |
| | 1426 | 1.411 | 0.160 | 0.122 |
| | 1440 | 0.370 | 0.145 | 0.170 |
| *B. abortus* | J3 | 2.311 | 0.355 | 0.309 |
| Infected | 25 | 3.730 | 1.451 | 1.641 |

TABLE 7-continued

| Comparison of Different Antigens[a] | | | | |
|---|---|---|---|---|
| | Labora- | ANTIGEN | | |
| Cattle Test Serum | tory Desig- nation | *B. abortus* 1119-3 sLPS | *B. abortus* 1119-3 O-chain | *Y.enterocolitica* 0:9 O-chain |
| | 44133 | 3.317 | 1.095 | 0.900 |

[a]Stored 2 weeks in 0.06M sodium carbonate buffer (pH 9.6)

[b]Readings are for $A_{414nm}$. Data <0.300 is negative, ≧0.300 is positive (note that there are no positives for vaccinate sera tested with O-chains as antigens, and that sera from infected cattle give comparable positive readings on these antigens)

A suitable concentration of antigen for coating appears to be in the range of about 1 to 5 μg/ml of O-chain for binding to polystyrene plates in the enzyme immunoassay, with an optimum concentration around 2.5μ g/ml. Lower concentrations cause decreased sensitivity, while higher concentrations give false positive results.

In carrying out step 4 of Table 2 above, a crude autoclave preparation of O-chain from *B. abortus* 1119-3 was extracted with phenol-water. The O-chain was found in the phenol-phase (in the highly pure form as judged by optical rotation), interphase (contaminated with sLPS as judged by ultracentrifugation characteristics) and water-phase (contaminated by nucleic acids as judged by high $A_{260nm}$ readings). The phenol-phase antigen worked as before, the interphase antigen gave high readings for vaccinates and culture-positive cattle sera, and the water-phase antigen gave low or negative readings for all sera tested. Therefore, the use of only purified O-chain from *B. abortus* is recommended.

The purified O-chain from *B. abortus* 1119-3 exhibits good shelf stability. For example, samples were stored for 1 year at −20° C., 6 months at room temperature in a closed vial, and 3 months in saline at 4° C. There were no discernible differences in results between these three antigens when applied to the test as described above. Recommended procedure is lyophilization, storage at −20° C. or colder, and prepared fresh when needed.

The procedures mentioned above are indirect tests, whereby the amount of antibody (bound to antigen coated polystyrene plates) is assayed by a colour change, e.g. anti-bovine antibodies conjugated with horseradish peroxidase act on hydrogen peroxide which reduces the chromogen ABTS (2,2'-azinodi-(3-ethylbenz-thiazolidine-sulfonic) acid). The colour change is time dependent, and optimal incubations for the test system have been found to be about 10 minutes. However, even with immunoassay absorbance readings taken at 70 minutes, or one hour past the optimum incubation, although both the negative sera, on either sLPS or O-chain antigens, and vaccinates sera, on the O-chain antigen, have given some reaction over this length of time, differentiation of these from *B. abortus* culture-positive sera is still easily made. Therefore, there is flexibility when using the present test system.

Sera from cattle infected by cross-reacting organisms were also investigated. In a limited study using five cows, each was experimentally infected with *Y. enterocolitica* 0:9. Sera from these animals showed high titres against *B. abortus* as judged by standard serological methods. However, with the present enzyme immunoassay using sLPS/O-chain, these animals appeared as vaccinates or gave high reactions with sLPS and negative reactions with *B. abortus* O-chain. This increased specificity is a means of differentiating cattle infected with *B. abortus* or cross-reacting organisms. The results are shown in the following Table 8.

TABLE 8

Comparison by an Enzyme Immunoassay of Sera from Cattle Infected by Different Bacteria

| Cattle Test Serum | Laboratory Designation | ANTIGEN *B abortus* 1119-3 sLPS | *B. abortus* 1119-3 0-chain |
|---|---|---|---|
| Negative Controls | 280 | 0.11[a] | 0.09 |
| | 281 | 0.11 | 0.10 |
| | 282 | 0.21 | 0.10 |
| Cattle infected | CF80 | >2.00 | 0.59 |
| with *B. abortus* | 25 | >2.00 | 1.45 |
| | 908 | >2.00 | 0.59 |
| | 44133 | >2.00 | 1.10 |
| Cattle experimentally | 518 | >2.00 | 0.08 |
| infected with *Y.* | 523 | >2.00 | 0.07 |
| *enterocolitica* 553 | >2.00 | 0.11 | |
| | 577 | >2.00 | 0.15 |
| | 582 | >2.00 | 0.09 |

[a]Readings are for $A_{414nm}$. Data <0.30 is negative, >0.30 is positive (note that only *B. abortus* infected cattle sera gives positive results on *B. abortus* 0-chain as antigen)

It should be noted that cattle that are either recently infected by *B. abortus* or have low numbers of the organism localized in a tissue may not have sufficient antibody titres to register as positive on this test. However, this is a limitation shared by other serological tests currently used to detect *B. abortus.*

While the use of polystyrene plates has been described above, other technologies, such as dipsticks or beads coated with *B. abortus* O-chain, are also effective in the differentiation of sera and can be employed.

Another example of an immunoassay is competitive binding assay utilizing the following principles. Polystyrene microtitre plates are coated with desired antigen (e.g. one set of wells with *B. abortus* 1119-3 O-chain). A mouse monoclonal antibody (e.g. Ys-T9-2) conjugated with an indicator enzyme (e.g. horseradish peroxidase) is then added. The plate is washed, test sera (e.g. from cattle) are added, incubated and then excess is removed by washing. If the test sera have antibodies of high affinity for the antigen, these will displace the mouse monoclonal antibody, decreasing the $A_{414nm}$ when substrate-chromogen (e.g. $H_{2}O_{2}$-ABTS) is added. If the test sera lack antibodies with such affinity, no such displacement occurs and when substrate is added the $A_{414nm}$ will be high.

Results showing the effectiveness thereof are shown in the following Table 9.

TABLE 9

Comparison of the Indirect ELISA and the Competitive ELISA

| Cattle Test Serum | Laboratory Designation | Indirect ELISA[a] Using *B. abortus* 1119-3 sLPS | Compet**i**ve ELISA[b] Using *B. abortus* 1119-3 0-chain |
|---|---|---|---|
| Negative | N1 | 0.07[c] | 1.72[c](0%)[d] |
| Control | N4 | 0.13 | 1.73 (0%) |
| | N5 | 0.12 | 1.73 (0%) |
| | N6 | 0.10 | 1.65 (3%) |
| Vaccinates | 446 | >2.00 | 1.54 (9%) |
| | 542 | 0.66 | 1.61 (5%) |
| | 679 | 1.56 | 1.64 (4%) |
| | 743 | >2.00 | 1.61 (5%) |
| | 1426 | 1.33 | 1.61 (5%) |
| | 1429 | 1.19 | 1.70 (0%) |
| | 1440 | 1.88 | 1.54 (9%) |
| *B. abortus* | 25 | >2.00 | 0.16 (90%) |
| Infected | 44133 | >2.00 | 0.21 (88%) |
| | 950 | >2.00 | 0.19 (89%) |
| | TAR | >2.00 | 0.34 (80%) |

TABLE 9-continued

Comparison of the Indirect ELISA and the Competitive ELISA

| Cattle Test Serum | Laboratory Designation | Indirect ELISA[a] Using *B. abortus* 1119-3 sLPS | Competive ELISA[b] Using *B. abortus* 1119-3 0-chain |
|---|---|---|---|
| | J2 | >2.00 | 0.51 (70%) |
| | J3 | >2.00 | 0.56 (67%) |

[a]The Indirect ELISA is that used in Tables 1 to 7 above. The above data gives insight into ani-Brucella titres for <0.30 is negative, ≧0.30 is positive.

[b]For the Competitive ELISA, see preceding description. Mouse monoclonal antibody Ys-T9-2 was conjugated with the enzyme horseradish peroxidase. Data in brackets indicates percent inhibition (i.e. displacement of conjugated monoclonal antibody) by applied sera antibodies. Calculations were done by:

$$\frac{\text{Control (1.70 as average)} - \text{Test Reading}}{\text{Control (1.70 as average)}}$$

Note that only *B. abortus* infected sera give significant displacement of monoclonal antibody.

[c]Readings are $A_{414nm}$

[d]Percent Inhibition

Moreover, while the use of the polysaccharide O-chain to differentiate vaccinated animals from infected ones has been described above primarily with reference to cattle and *B. abortus*, the use of the polysaccharide O-chains of *Brucella spp.* (or of cross-reacting organisms) in swine, goats, sheep and humans may be expected to follow the same model, as might other animal or human diseases, and is considered to be within the scope of the invention.

What is claimed is:

1. A method for discriminating between (i) normal animals or animals vaccinated or immunized against smooth Brucella sp. or *Y. enterocolitica* 0:9, and (ii) animals infected with smooth *Brucella sp.* or *Y. enterocolitica* 0:9, comprising the steps of:

(a) subjecting serum samples from the animals to immunoassay to detect serological activity against an O-chain polysaccharide containing 4,6-dideoxy-4-acylamido-D-mannopyranose repeating units; and (b) differentiating the sera of the normal animals or vaccinated or immunized animals from those of infected animals based on a negative or positive result, respectively, of said assay, wherein the sera from infected animals is differentiated from the sera of normal animals or vaccinated or immunized animals based on the differences in specificity or affinity between antibodies of infected animals and antibodies of normal animals or vaccinated or immunized animals to said O-chain polysaccharide.

2. A method according to claim 1, wherein the animals are cattle.

3. A method according to claim 1, wherein the immunoassay technique comprises enzyme immunoassay.

4. A method according to claim 1, wherein the polysaccharide has been obtained from O-chains of strains of *B. abortus, B. melitensis* or *Yersinia enterocolitica.*

5. A method according to claim 1, wherein the purified O-chain polysaccharide has been obtained from *B. abortus* 1119-3 or *B. abortus* 413, *Y. enterocolitica* 0:9 or *B. melitensis* 16M.

6. A method according to claim 1, wherein the polysaccharide contains 4,6-dideoxy-4-formamido-D-mannopyranose units.

7. A method according to claim 1, wherein said *Brucella sp.* is *Brucella abortus*, said animals are cattle, and said O-chain polysaccharide is of *B. abortus* and contains 4,6-dideoxy4-formamido-D-mannopyranose repeating units.

8. A method according to claim 1, wherein the immunoassay technique comprises agar gel immunodiffusion (AGID), indirect or competitive enzyme immunoassay (ELISA), competitive immunoassay, radioimmunoassay, immunofluorescent assay, or immunoassay using polystyrene plates, membranes, dipsticks or beads.

9. A method according to claim 1, wherein the immunoassay is an ELISA procedure carried out using as antigen the polysaccharide bound to polystyrene plates.

10. A method according to claim 9, wherein the concentration of the antigen is from about 1 to 5 $\mu g/ml$.

11. A test kit for carrying out an immunoassay for discriminating between animals vaccinated or immunized against those infected with smooth Brucella sp. or *Y. enterocolitica* 0:9, comprising:

(a) a solid support having fixed thereon an O-chain polysaccharide containing 4,6-dideoxy-4-acylamido-D-mannopyranose units; and (b) means for discriminating immunologically between the presence or absence of antibodies against smooth Brucella sp. or *Y. enterocolitica* 0:9.

12. The test kit according to claim 11, wherein said Brucella sp. is *Brucella abortus*, said animals are cattle, said O-chain polysaccharide is of *B. abortus* and contains 4,6-dideoxy-4-formamido-D-mannopyranose repeating units and said means are reagents for an enzyme-linked immunoassay.

13. A test kit according to claim 12, and including polylonal antibodies or monoclonal antibodies.

* * * * *